(12) United States Patent
Hair

(10) Patent No.: US 6,355,044 B1
(45) Date of Patent: *Mar. 12, 2002

(54) EXPANDABLE BONE CONNECTOR

(76) Inventor: John Hunter Hair, 122 Haddonfield La., Cary, NC (US) 27513

( * ) Notice: Subject to any disclaimer, the term of this patent is extended or adjusted under 35 U.S.C. 154(b) by 0 days.

This patent is subject to a terminal disclaimer.

(21) Appl. No.: 09/633,975

(22) Filed: Aug. 8, 2000

Related U.S. Application Data

(63) Continuation of application No. 09/292,286, filed on Apr. 15, 1999, now Pat. No. 6,126,663.

(51) Int. Cl.[7] .............................................. A61B 17/56
(52) U.S. Cl. ..................................................... 606/72
(58) Field of Search .............................. 606/72, 69, 53, 606/232, 75, 104, 73, 74; 411/495, 25, 26, 44, 45, 57.1, 60.2, 63, 72, 55, 80.2, 33, 913

(56) References Cited

U.S. PATENT DOCUMENTS

| | | | | |
|---|---|---|---|---|
| 2,199,271 A | * | 4/1940 | Schaefer ..................... | 411/80.2 |
| 2,301,244 A | * | 11/1942 | Bishop ....................... | 411/80.2 |
| 2,340,423 A | * | 2/1944 | Oshaughnessy et al. ... | 411/80.2 |
| 2,353,851 A | * | 7/1944 | Rosan ........................ | 411/80.2 |
| 2,826,110 A | * | 3/1958 | Lemelson ................... | 411/80.2 |
| 3,099,931 A | * | 8/1963 | Ferdinand ................... | 411/15 |
| 3,213,745 A | * | 10/1965 | Dwyer ......................... | 411/15 |
| 4,263,833 A | * | 4/1981 | Loudin et al. ................. | 411/41 |
| 4,405,272 A | * | 9/1983 | Wollar ......................... | 411/41 |
| 5,259,689 A | * | 11/1993 | Arand et al. .................. | 403/337 |
| 5,707,373 A | * | 1/1998 | Sevrain et al. ................ | 606/72 |

* cited by examiner

*Primary Examiner*—Gary Jackson
*Assistant Examiner*—(Jackie) Tan-Uyen T. Ho
(74) *Attorney, Agent, or Firm*—Coats & Bennett, P.L.L.C.

(57) ABSTRACT

An expandable fastener is used to join adjacent portions of bones for surgical recovery. The fastener typically includes a sleeve having an expandable section and a ram that is moveable between a ready position and a deployed position. When the ram is moved to the deployed position, the ram forces the sleeve to expand against at least one of the bone sections. Preferably, the sleeve includes a plurality of prongs in the expandable section that are forced outwardly when the ram is moved to the deployed position. The prongs may include protrusions having bearing surfaces that curve outwardly from the bore of the sleeve. When the sleeve is expanded, the protrusion bearing surfaces apply both a lateral and a radial force, with the radial force acting to clamp one or both of the bone portions between the prong and a flange on the sleeve. In some embodiments, the fastener is designed to be shorter than the surrounding bone is thick so that the fastener may be used to secure adjacent bone sections without extending into the cranial cavity. A method of using the fastener is also disclosed wherein a fastener is inserted into at least one craniotomy burr hole and thereafter expanded, such as by driving the ram of the typical fastener down into to sleeve by screwing the ram into the sleeve. All burr holes may be filled by a fastener, thereby providing multi-point fixation of the bone flap to the surrounding cranial bone.

8 Claims, 5 Drawing Sheets

EXPANDABLE BONE CONNECTOR

This is a continuation of application Ser. No. 09/292,286, filed Apr. 15, 1999, now U.S. Pat. No. 6,126,663.

FIELD OF THE INVENTION

This invention relates to a method of joining two adjacent portions of bone, for example, when replacing a portion of the cranial vault removed during a craniotomy.

BACKGROUND OF THE INVENTION

In most neurosurgical and cranial operations, it is necessary to open a large access hole in the skull by forming a segment of the skull, called a bone flap, which is then bent out of the way or broken out from the surrounding skull. To form the bone flap, several holes are typically drilled through the skull, commonly referred to as burr holes. The burr holes are then connected by osteotomy cuts, for example using a Gigli flexible saw which is passed internally between the burr holes. The saw is then oscillated back and forth to cut the skull along a line connecting adjoining burr holes. The position, number, and size of the burr holes drilled through the skull, as well as the number of connecting osteotomies, is determined by the size, location and geometrical form of the desired bone flap and corresponding access hole. For example, if the bone flap to be removed is a triangular skull cap segment, three holes are preferably drilled at the corner points of the bone flap, connecting osteotomies are made along the sides of the curved triangle delineated by burr holes, resulting in a triangular segment bone flap. The bone flap is subsequently lifted off the underlying dura mater to expose the brain for the further steps of the operation. The bone flap may either be completely removed from the surgical site, or folded back along an uncut edge.

At the end of the procedure, the previously removed bone flap or flaps are repositioned into their original locations, or in different desired locations, relative to the surrounding bone portions. This is typically accomplished in the prior art by drilling small pairs of holes in the surrounding skull bone in several places around the edge of the bone flap. Wire is then carefully threaded through the holes, taking care not to tear the dural tissue covering the brain, then twisted together to secure the edges, the ends tucked into the cut opening so that they do not puncture the skin, and the skin then stitched into place over the skull flap. The procedure is complex and time consuming, and there always is the possibility of injuring the dura either by using the high speed drills that are necessary to form the small holes or by the sharp points of the wire engaging the dura.

Other known methods for providing fixation between adjacent bone portions have included the use of metallic plates of varying configurations which are secured across osteotomies or fracture sites by metallic bone screws. Other devices, such as intramedullary nails or externally fixed pins, have also been used to reduce bone fracture mobility and to improve the relative position of adjacent segments. See for instance U.S. Pat. No. 5,669,912 to Spetzler. The aim of fixation of adjacent bone portions is to immobilize the fracture or osteotomy sites in order to promote localized bone growth in the natural repair of the separation.

A brief survey of prior art methods may be found by looking at patents previously issued on the subject. For instance, U.S. Pat. No. 5,201,737 discloses a flexible plate having a plurality of vanes with holes for receiving bone screws. The plate is placed over a cranial burr hole and adjoining osteotomy lines to provide external fixation of the bone flap to the surrounding cranium. Other external bone plates are shown in U.S. Pat. Nos. 4,651,724; 4,923,471; 5,139,497; 5,372,498; and 5,578,036. All of these plates are designed for external application to fractured bones and require placement of a plurality of screws through the plates and into the bone. Placement of multiple screws through the plates is time consuming, induces additional trauma in drilling the pilot holes for the screws, and may predispose the site to infection.

Other fixation devices are also known, such as the device shown in U.S. Pat. No. 2,511,051 which involves screwing an externally threaded stud into an internally threaded shank. Movement of the stud into the shank is guided by an hexagonal wrench that is inserted through the shank into a countersunk receptacle on the tip of the threaded stud. A similar device is shown in U.S. Pat. No. 5,707,373. These devices have proved cumbersome to use. Further, these devices necessarily require that a portion of the fastener be disposed on both the inner and outer surfaces of the bone, thereby exposing the dura matter of the brain to direct intimate contact with the fastener.

In spite of the use of a variety of fasteners in surgical procedures, improved techniques are still being sought to secure adjacent portions of bone for healing, particularly for securing bone flaps to the surrounding cranium following a craniotomy.

SUMMARY OF THE INVENTION

The present invention utilizes an expandable fastener, called a bone lock, to join adjacent portions of bones for surgical recovery. The bone lock includes main body having an expandable section and an expansion driver. Moving the expansion driver from a first position to a second position forces the expandable section to expand, thereby causing the bone lock to engage the nearby bone material.

One preferred embodiment of the bone lock includes a sleeve having an expandable section and a ram that is moveable between a ready position and a deployed position relative to the sleeve. When the ram is moved to the deployed position, the ram acts against the sleeve to expand the sleeve's expandable section. When expanded in a burr hole, the sleeve is forced against at least one of the bone sections, thereby constraining the relative motion between the bone portions.

Preferably, the sleeve includes a plurality of prongs in the expandable section. These prongs are forced outwardly when the ram is moved to the deployed position. In most embodiments, the prongs include protrusions having bearing surfaces that curve outwardly from the bore of the sleeve. When the sleeve is expanded, bearing surfaces on the protrusion preferably act against the bone to hold the bone lock securely against the bone. Preferably, the bearing surfaces apply both a lateral and a radial force, with the radial force acting to clamp the bone between the prong and a flange on the sleeve. The bone lock may clamp only one of the bone portions with such an embodiment, but it is preferred that the bone lock clamp onto both bone portions.

Further, in some embodiments, the bone lock is designed to be shorter than the surrounding bone is thick. With such embodiments, the bone lock may be used to secure adjacent bone sections without extending into the cranial cavity by instead extending into the medullary layer of the surrounding bone portions.

During the closure portion of a typical craniotomy, the bone flap is appropriately positioned in the craniotomy opening and a bone lock is inserted into at least one of the burr holes formed earlier in the craniotomy. The bone lock described above is expanded by driving the ram down into to sleeve, typically by screwing the ram into the bore of the sleeve. The movement of the ram forces the sleeve to expand, thereby restricting the relative motion of the two bone portions. Ideally, the bone portions are secured both laterally (approximately along the skull surface) and radially (generally normal to the skull surface) by the bone lock. Further, while it is not required, it is preferred that all burr holes be filled by a bone lock, thereby providing multi-point fixation of the bone flap to the surrounding cranial bone.

The use of the present approach allows the bone sections to be joined without the creation of additional holes in the skull or bone flap, particularly small screw holes, thereby saving time and reducing the risk of infection. In addition, the use of the optional shorter bone lock embodiments allows the bond flap to be secured without having portions of the fasteners protruding into the cranial cavity, thereby lessening the risk of injury to nearby soft tissue, such as the brain's dura matter.

DETAILED DESCRIPTION

Figure 1:
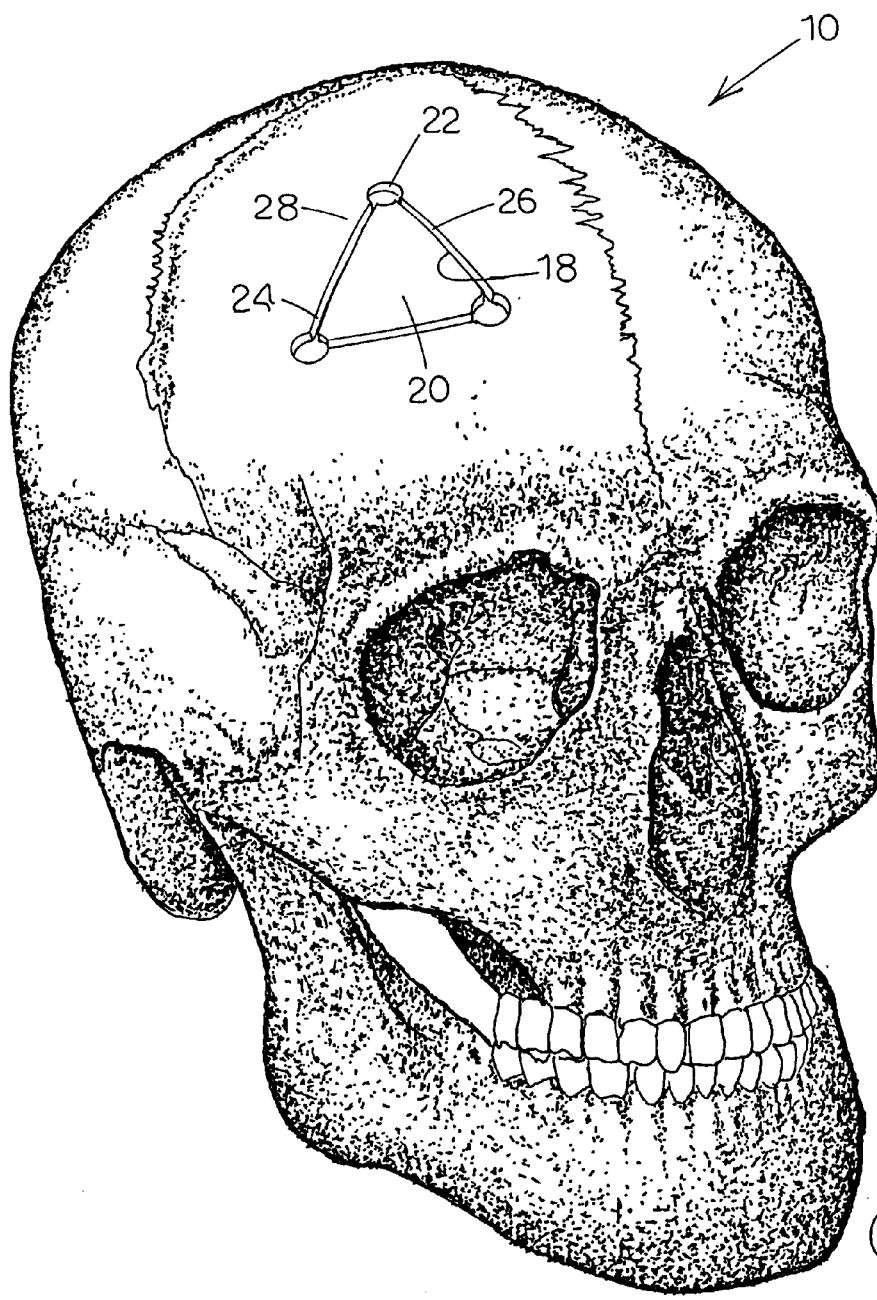
FIG. 1 is representative view of a human head showing one possible location and configuration of a craniotomy bone flap.
Figure 3:
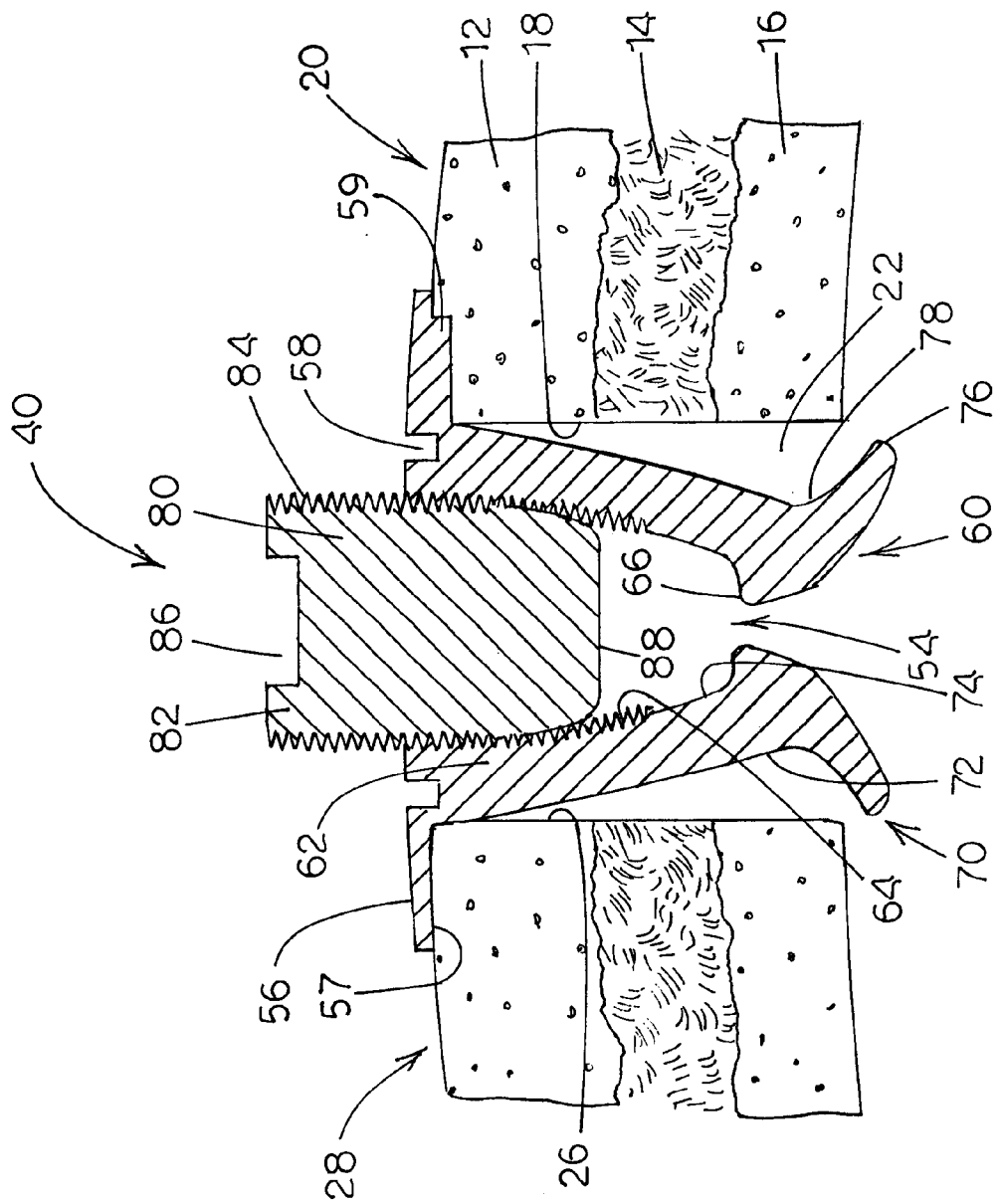
FIG. 3 is a sectional view of one embodiment of a bone lock inserted in a burr hole prior to expansion with the ram in the ready position.
Figure 4:
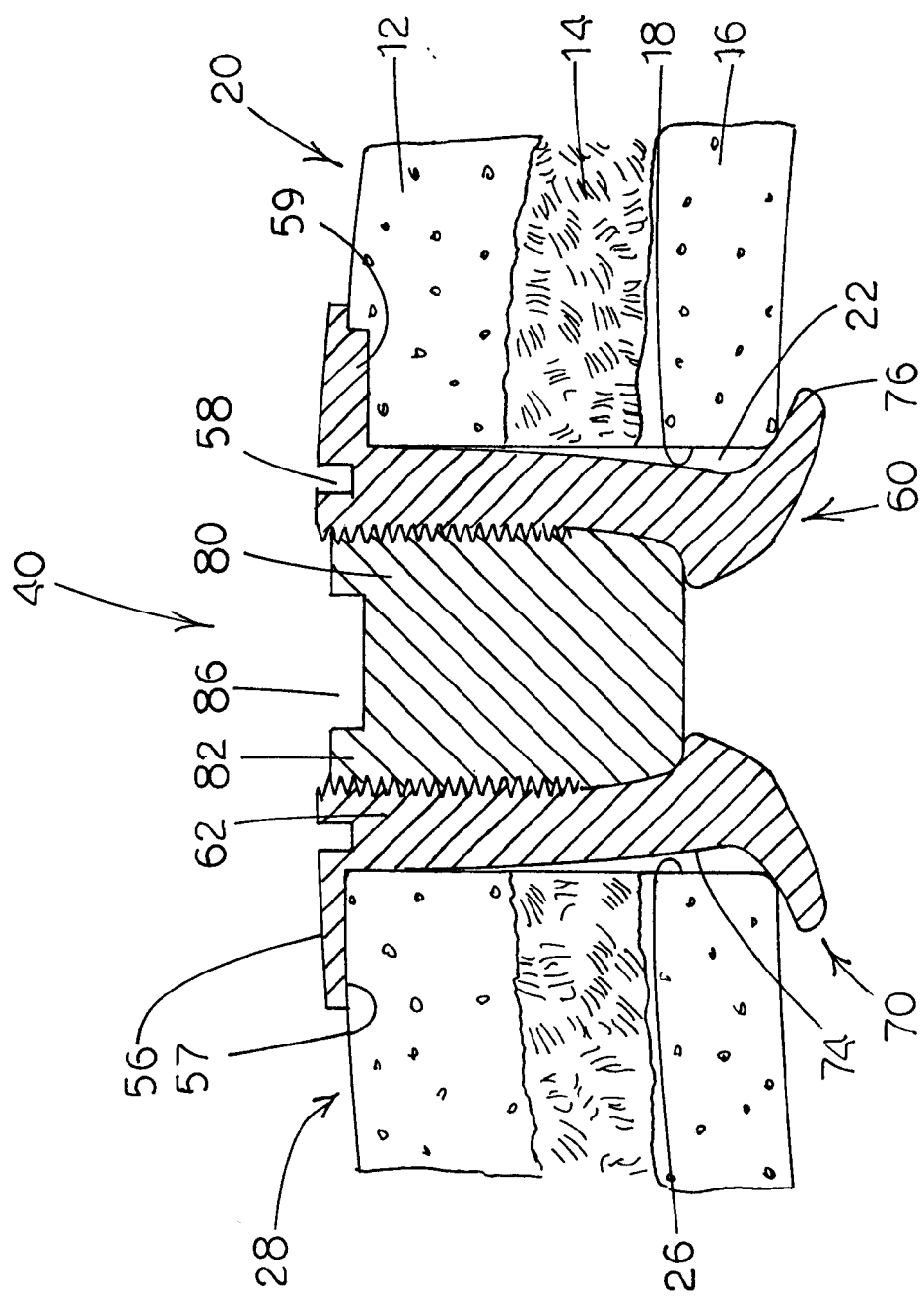
FIG. 4 is a sectional view of the bone lock of FIG. 3 after expansion with the ram in the deployed position.
Figure 5:
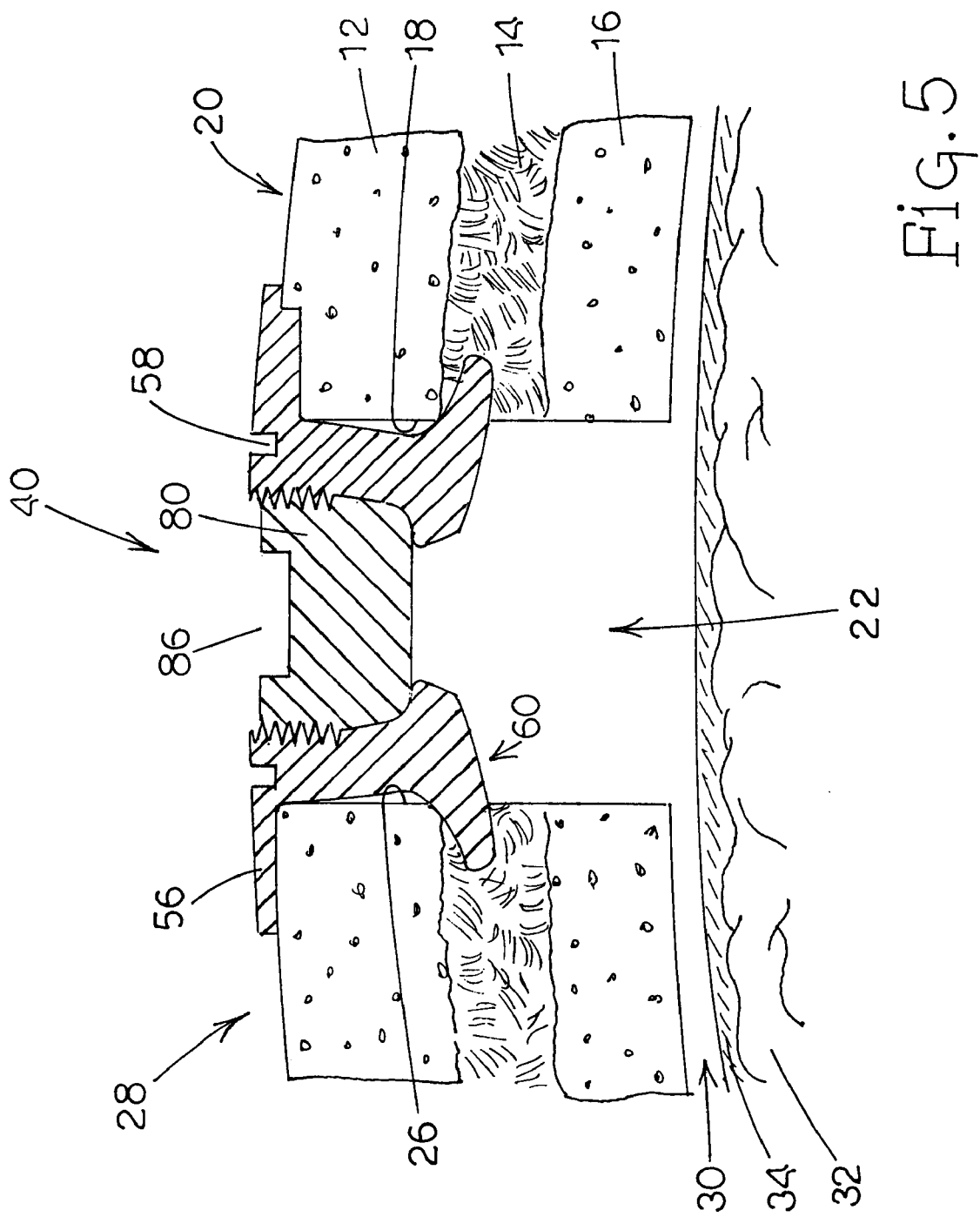
FIG. 5 is a sectional view of another embodiment of the bone lock with shorter prongs after expansion in a burr hole showing engagement of the cancellous bone layer and the underside of the outer cortical bone layer by the protrusions.

For reference, a human skull 10 with a craniotomy bone flap 20 is shown in FIG. 1. The bone flap 20 is defined by three burr holes 22 and the connecting osteotomy cuts 24. As pointed out above, the bone flap 20 need not be of the particular shape shown and may have any number of burr holes 22. On the opposing sides of the osteotomy cuts 24 are the respective bone edge surfaces 18,26 of the bone flap 20 and the surrounding bone 28 of the skull 10, respectively. See FIG. 3. The skull 10 and bone flap 20 are made from bone that can be considered to have a three layer composition, as shown in FIGS. 3–5. The outermost layer is the outer cortical bone 12 and the innermost layer is the inner cortical bone 16. Between these two relatively stiff layers is a relatively soft middle layer known as the cancellous bone 14. Interior to the inner cortical bone 16 is the cranial cavity 30 housing the brain 32 and its surrounding dura matter 34. While FIG. 1 shows a completely surgically-created bone flap 20, it is to be understood that the bone flap 20, including the burr holes 22 and the cut lines 24, may be formed by other means, such as by impact trauma and the like.

The present invention utilizes at least one, and preferably a plurality of, expandable bone locks 40 to join together two adjacent portions of bone 20,28. The approach is particularly adapted for securing craniotomy bone flaps 20 to the skull 10, but may be used in other situations where appropriate.

The present illustrative discussion will assume that the bone lock 40 is being used to close a typical triangular craniotomy bone flap 20 having three burr holes 22, one at each apex, connected by thin osteotomy cuts 24 which may be normal to the surface of the skull 10 or at an angle thereto.

Figure 2:
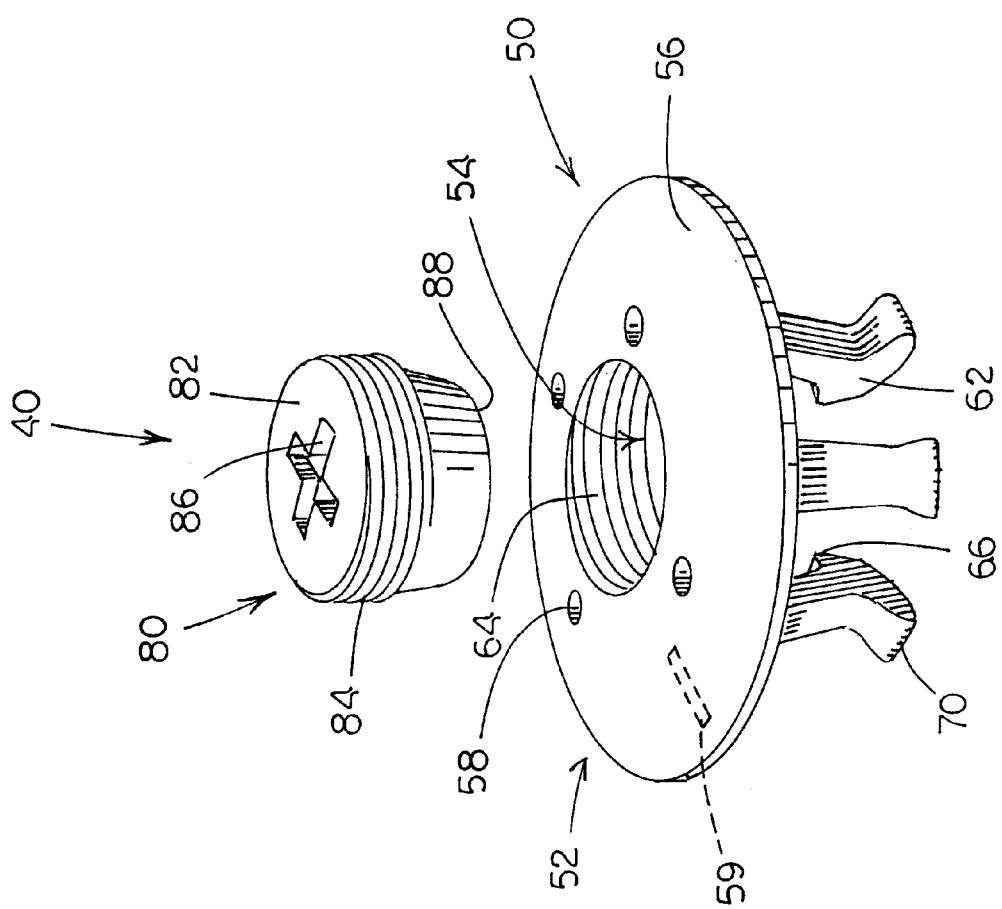
FIG. 2 is a perspective view of one embodiment of a bone lock of the current invention.

For the embodiment illustrated in FIGS. 2–4, the expandable bone lock 40 includes a ram 80 and an expandable sleeve 50. The ram 80 is preferably a generally cylindrical shaped body having a lower tip 88 and an upper head 82. The lower tip 88 is preferably tapered, chamfered, or radiused on its end so as to provide a reduced diameter section smoothly followed by a larger diameter section. The outer surface of the ram 80 preferably includes threads 84 for mating with corresponding threads 64 on the upper portion of the sleeve 50 as described more fully below. The head 82 preferably includes an indentation 86 or other means for accepting a driver, such as a Phillips head screwdriver. The lower tip 88 of the ram 80 preferably has a radiused edge for pushing against the spur 66 of the sleeve 50 as discussed below. The ram 80 should be made from suitably hard material so as to resist the compressive forces exerted by the sleeve 50 without collapsing or significantly deforming.

The sleeve 50 includes a main body with a head 52 at one end and a plurality of prongs 60 at the other and generally defining an opening, referred to herein as a bore 54. The sleeve 50 should have a perimeter that sweeps at least 180°, and preferably a full 360° as shown in FIG. 2. The bore 54 may be offset from the center of the sleeve 50, but the bore 54 is preferably along the central axis of the sleeve 50. The head 52 is wider than the burr hole 22 in at least one direction so as to prevent the sleeve 50 from being inserted through the burr hole 22. While the head 52 may include discrete tab flanges, partial collars, wings, or the like, that extend outwardly from the bore 54, the head 52 preferably includes a continuous annular flange collar 56 as shown in FIG. 2. Further, while the sleeve 50 is preferably round, the sleeve 50 may take on a wide variety of shapes, such as triangular, trapezoidal, irregularly lobed, etc. Obviously, it is preferred that general shape of the sleeve 50 be similar to the shape of the corresponding burr hole 22.

In some embodiments, the flange 56 of the sleeve 50 includes an optional means to help prevent relative rotational motion between the sleeve 50 and the surrounding bone 28 while the ram 80 is being moved into the sleeve 50. For instance, the underside 57 of the flange(s) 56 may include a plurality of downwardly extending gripping bumps (not shown) that are designed to slightly bite into the outer surface of the surrounding bone and the bone flap 20. Other gripping means approaches include adding one or more registration guides 59 that are designed to fit into the associated osteotomy cuts 24 to the underside 57 of the flange(s) 56. Or, the flange(s) 56 may include a plurality of grip holes 58 that are designed to accept corresponding installation tool retention fingers that remain stationary while a center drive element of the tool engages the ram 80. In short, any known means of retaining the sleeve 50 in position may be used if so desired.

For the embodiment of FIGS. 2–5, extending downwardly from the head 52 are a plurality of prongs 60. The sleeve 50 may have two or more prongs 60; however, it is believed that the sleeve 50 should have at least three prongs 60 for optimal stability in use. The sleeve 50 shown in FIG. 2 has six prongs 60. The prongs 60 may take a variety of shapes, but in most embodiments the prongs 60 include a downwardly extending leg 62 with outwardly extending protrusion 70 on a lower exterior portion 72 thereof. The combination of the interior surfaces 74 of the legs 62 help define the bore 54.

Preferably, threads 64 are provided along at least a portion of the interior surfaces 74 of the legs 62 for mating with the ram 80 as described more fully below. The protrusion 70 preferably includes a curved bearing surface 78 on its upper exterior portion and a small radius rounded tip 76. The lower portion of protrusion 70 may be of almost any shape, but is preferably relatively flat or slightly concave.

The lower interior surface of the legs 62 preferably include a spur 66 that extends inwardly to the bore 54, thereby locally reducing the local effective diameter of the bore 54. The upper portion of the spur 66 is preferably curved to allow for a sliding interface with the top of the ram 80. Alternatively, the interior diameter of the bore 54 may be gradually reduced by sloping the interior surfaces 74 of the legs 62 inwardly, such as by varying the nominal radial thickness of the leg 62, or by any other approach known in the art. The basic requirement is that the lower portion of the bore 54 have a reduced dimension before the ram 80 is present, so that introduction of the ram 80 into the lower portion of the bore 54 causes the bore 54 to expand, thereby pushing the protrusions 70 outwardly.

To use the bone lock 40, the initial steps of the craniotomy are performed in the usual fashion. When the cranial cavity is ready to be closed, an un-expanded bone lock 40 is arranged in each of two of the three burr holes 22. Because the bone flap 20 is not yet present, these bone locks 40 may need to be held in place by gentle finger pressure. However, it is believed that the bone locks 40 will likely be supported in place by the surrounding bone 28 of the skull 10 because only a limited circumferential portion of the burr hole 22 will be missing (as part of the bone flap 20 and osteotomies 24). Thereafter, the bone flap 20 is put in place and the third bone lock 40 is inserted into the third burr hole 22. Alternatively, the bone flap 20 may be put in place and then the three bone locks 40 may be inserted into the three burr holes 22. It should be noted that in the un-expanded state, the sleeves 50 should just fit into their corresponding burr holes 22. For instance, the outermost portion of the prongs 60 should be disposed inwardly enough so that the prongs 60 may easily slide into the corresponding burr hole 22 as shown in FIG. 3. At insertion of the sleeve 50, the ram 80 may be separate from the sleeve 50 or may be partially mated therewith; preferably, the ram 80 is slightly screwed into the sleeve 50. For ease of reference, the position of the ram 80 prior to expansion will be referred to as the "ready position."

With the bone flap 20 and bone locks 40 in place, the rams 80 are driven into their respective sleeves 50, thereby forcing the prongs 60 of the respective sleeves 50 to expand outwardly. As the ram 80 is screwed into the sleeve 50, the tip 88 of the ram 80 travels downwardly. At some point along its travel, the tip 88 begins to engage the spur 66. Because the diameter of the ram 80 is larger than the pre-expansion diameter of the bore 54 in the vicinity of the spurs 66, the ram 80 acts against the spurs 66 to push the prongs 60 outwardly. See FIG. 4.

To facilitate the relative motion between the ram 80 and the spurs 66, respective curved surfaces are provided as described above. As the prongs 60 are forced outwardly, the corresponding protrusions 70 are brought into contact with, and act against, the nearby bone edges 18,26. Where the prongs 60 are of such length that the protrusions 70 are disposed below the inner cortical layer 16, the protrusions 70 act against the inner cortical layer 16. In most embodiments, the curved bearing surface 78 engages the edge 26 of the bone 28. The outward action of the protrusions 70 helps secure the bone lock 40 in place. In addition, the force applied by the bearing surface 78 also acts to clamp the bone 28 between the protrusions 70 and the flange(s) 56. Preferably, the bearing surfaces 78 are designed so that most of the force generated by the bearing surfaces 78 is the clamping force acting in conjunction with the flange 56, rather than pure outward force. For ease of reference, this lower position of the ram 80, with the sleeve 50 of the bone lock 40 expanded to engage one or the other, or both, of the bone portions 20, 28, will be referred to as the "deployed position." It should be noted that being in the deployed position does not necessarily require that the ram 80 be fully lowered into the bore 54. However, length and configuration of the ram 80 may optionally be selected so that the top of the ram 80 is lower than, or flush with, the top of the flange 56 when the ram 80 is fully inserted. Such an arrangement should provide a better cosmetic appearance.

As will be appreciated by those in the art, the described bone lock 40 preferably directly engages both the bone flap 20 and the surrounding bone 28 of the skull 10 around the burr hole 22. That is, while the bone lock 40 may directly engage only one or the other, the bone lock 40 preferably directly engages both bone portions 20,28 simultaneously. Further, an individual prong 60 may directly engage the bone flap 20, the surrounding bone 28 of the skull 10, or both.

The bone locks 40 may be expanded in any sequence, but they are preferably gradually expanded in an iterative series. When the bone locks 40 are sufficiently expanded, the surgical closure procedure continues in the typical fashion. The interaction of the bone locks 40 holds the bone flap 20 in place. The expansion of the bone locks 40 helps make up the bone material lost during the formation of the burr holes 22, therefore, no anchor screws are needed, such as with the approach of Stone et al. (U.S. Pat. No. 5,578,036).

Preferably, the shape of the respective interacting surfaces of the ram 80 and the spurs 66 provide a stop to help prevent over-insertion of the ram 80. For instance, the bone lock 40 of FIG. 4 shows the ram 80 in a deployed position where the tip 88 of the ram 80 is butting against the spurs 66. While it may be possible to over-insert the ram 80 for such an embodiment, it would likely require significantly more force because of the almost horizontal nature of the inward-most portion of the spur 66. This arrangement is thought to provide sufficient feedback to the user to help prevent over-insertion.

While the discussion above has assumed that three bone locks 40 are used, such is not a requirement of the invention. Indeed, the present approach works when only a single bone lock 40 is used. For instance, the bone flap 20 may be placed in the skull opening without any bone locks 40 in place. Thereafter, as few as one of the burr holes 22 may be filled with a bone lock 40 and that bone lock 40 expanded as described above. This expansion action should displace the bone flap 20 away from the filled burr hole 22 and up against the opposing cut surface 26 of the skull 10. The remaining burr holes 22, if any, may be covered by any means known in the art, such as with the metal plates of the prior art, or left uncovered. However, it is believed that a safer and more stable approach is to use multiple bone locks 40. The use of three or more bone locks 40 approximately equally spaced around the bone flap 20 should allow the bone flap 20 to be securely held in place both laterally (roughly parallel to the outer surface of the surrounding bone) and radially (into or out of the cranial cavity, generally normal to the lateral direction) by the interaction of the bone locks 40. It should be noted that the present method is not limited to the use of three or fewer bone locks 40, but instead comprehends using any number of bone locks 40, although use of more than five would be unusual.

The discussion above has assumed that the ram 80 is driven downwardly through the bore 54 by screw action of the threads 64,84 associated with the ram 80 and the sleeve 50; however, such is not required. The particular method of moving, and retaining, the ram 80 is not important, and any method known in the art may be used. For instance, a method of gripping the flange 56 and pushing the ram 80 to drive it forward may be used. As another example, small ears (not shown) may be included on the ram 80 and corresponding L-shaped slots (not shown) included on the bore 54 of the sleeve 50 to allow the ram 80 to inserted and twist-locked into position. The ears would be aligned with the slots and to allow the ram 80 to be pushed into the bore 54 of the sleeve 50. When the ram 80 was inserted to the proper depth, the ram 80 could be twisted to force the ears into the short part of the L-shaped slots; with the ears so disposed, the ram 80 would be held in place by ears acting against the spring-like force of the prongs 60.

In addition, while the bone lock 40 is generally intended to be permanently installed, some or all of the bone lock 40 may be removed after installation, for instance to allow surgical re-entry. As an illustrative example, while it is strongly preferred that the ram 80 remain in place after reaching the deployed position, the ram 80 may instead be partially or totally removed from the sleeve 50. Or, the entire bone lock 40 may be removed after the osteotomies 24 have healed.

In some embodiments, the prongs 60 may be of such a length that the protrusions 70 are approximately level with the softer cancellous layer 14 of the skull 10 and bone flap 20, as shown in FIG. 5. In such embodiments, the protrusions 70 may be urged outwardly and into the cancellous bone layer 14. Preferably, the sleeves 50 in such embodiments are expanded to the point that the protrusions 70 engage the underside of the stiffer outer cortical bone 12, as shown in FIG. 5. Such shorter-pronged embodiments have the additional advantage of not extending below the inner cortical bone 16, thereby avoiding contact with the underlying dura 34 of the brain 32.

Alternative embodiments of the bone lock 40 do not have prongs 60 per se, but instead rely on some other configuration to allow the sleeve 50 to expand. For instance, a portion of the sleeve 50 may have a deformable Z-folded outer surface proximate the reduced size portion of the bore 54. Upon insertion of the ram 80 to the deployed position, the Z-folded surface would allow the sleeve 50 in that expandable section to expand and be forced against the bone portions forming the burr hole 22. In other words, the sleeve 50 would balloon out, but would remain contiguous in the expanded section.

In another alternative embodiment, the bone lock 40 employs a moveable wall section as its expandable section. For example, the main body of the sleeve 50 may have an incomplete perimeter that sweeps more than 180°, but less than 360°. The moveable wall section, referred to herein as the tongue, roughly completes the perimeter. The tongue is initially retracted into the main body of the sleeve 50, but moves outwardly away from the main body of the sleeve 50 to an expanded or deployed position. The tongue preferably includes its own flange and protrusions that act in concert with the flange 56 and protrusions 70 on the sleeve 50. The tongue may be driven to expand by any suitable expansion driver, such as the ram 80 of FIG. 2 or a suitable gear assembly. For instance assuming a gear assembly is used, the tongue may be moved to its deployed position by turning a central shaft associated with the sleeve 50. This shaft would include appropriate gearing on its lower portion that engages one or more worm gears on the interior portion of the tongue. By turning the shaft, the worm gear(s) force the tongue to move away from the sleeve 50 in a generally lateral direction and into firm contact with the nearby surrounding bone 28 and/or bone flap 20. Of course, the action of the tongue against the bone material also creates a reciprocal force that forces the main body of the sleeve 50 to likewise engage its nearby bone material.

It can be seen from the discussion above that whatever the embodiment, the bone lock 40 includes a main body 50 having an expandable section, such as the prongs 60 or the tongue, and an expansion driver, such as the ram 80, a gear assembly, a cam assembly, or other means that acts to expand the expandable section. When expanded, the bone lock 40 grips, clamps, or otherwise firmly contacts the nearby bone material so as to limit the relative motion between the bone flap 20 and the surrounding bone 28.

In either the pronged or non-pronged versions, the sleeves 50 may or may not have protrusions 70. Without protrusions 70, the sleeve 50 may be expanded to press laterally against the nearby bone 20,28 forming the burr hole 22, without necessarily digging into such bone 20,28. Such an arrangement is believed less desirable due to the absence of any outward radial stability (i.e., up away from the cranial cavity) except through friction between the sleeve 50 and the bone 20,28. Thus, it is believed to be advantageous for the bone lock 40 to include prongs 60 that engage one, and preferably both, of the bone portions 20,28 being joined on a lower surface.

The sleeve 50 and ram 80 may be made from a variety of materials, such as biocompatible metals like titanium, stainless steel, cobalt chrome molybdenum, and the like, and/or bioresorbable materials such as those referred to in U.S. Pat. No. 5,868,746. The selection of materials and dimensions for the various parts may be chosen to allow the prongs 60 to flex back once the ram 80 is removed or may be chosen so that the prongs 60 are permanently deformed by the ram expansion.

Preferably, the lower portion of the bone lock 40, in the un-expanded state, fits within a seven to ten millimeter diameter so as to fit in the most common burr hole size. Of course, other sizes may be used depending on the application. Further, the flange 56 is preferably relatively thin, such as one millimeter or less, with a overall width of five millimeters larger than the burr hole 22. The overall height of the bone lock 40 may vary widely, but distances of approximately two to fifteen millimeters between the protrusion 70 and the underside 57 of the flange 56 should accommodate most skulls 10, with dimensions of two to six millimeters being most appropriate for cancellous engaging bone locks 40.

The description above has used directional terms such as downwardly, upwardly, and the like for convenience to describe the present invention and its parts as oriented in the drawings. However it is to be understood that such terms are not intended to be limiting since such invention may obviously be disposed in different orientations when in use. Indeed, while it is not believed to be advantageous, the bone lock 40 may be inserted upside down (with the flange 56 inside the cranial cavity 30) and the ram 80 "pulled" radially away from the brain cavity 30 so as to expand the sleeve 50, rather than "pushed" radially towards the brain cavity 30.

The present invention is useful for joining adjacent sections of bone. Such adjacent sections typically do not overlap each other, but instead either abut or almost abut one another. Of course, there may be some small amount of overlap if, for instance, the osteotomy cut 24 defining the boundary between the portions is made at an angle that is offset from normal to the bone surface. However, it is intended that the adjacent portions of bone have their corresponding bone edges 18,26 lying generally along a lateral plane, rather than substantially vertically offset from one another.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of joining first and second bone portions using an expandable fastener, comprising:

positioning the first and second bone portions so as to be adjacent on along at least one edge;

forming at least one opening substantially defined by the adjacent bone portions;

inserting the expandable fastener into said opening; said fastener having an expandable section; and thereafter, with said bone portions adjacent to one another, expanding said expandable section into firm contact at least one of said first and second bone sections so as to constrain the relative motion between said first and second bone sections.

2. The method of claim 1 wherein said fastener includes an expansion driver moveable between a first position and a second position, and wherein said expanding includes moving said expansion driver from said first position to said second position.

3. The method of claim 2 wherein said fastener includes a sleeve having said expandable section and wherein said expansion driver includes a ram and wherein said expanding includes moving said ram relative to said sleeve.

4. The method of claim 3 wherein said moving includes screwing said ram into said sleeve.

5. The method of claim 1 wherein said opening defines a burr hole has a first size and wherein said expandable section includes a plurality of prongs that:

a) fit within a cylindrical space having a diameter smaller than said first size before said expansion; and b) extend outside a cylindrical space having a diameter at least as large as said first size after said expansion.

6. The method of claim 1 wherein said expandable section includes a plurality of prongs and wherein said expansion causes said prongs to engage both of said bone sections.

7. The method of claim 1 wherein at least one of said first and second bone sections is a portion of a skull having an inner cortical bone and wherein said fastener does not extend interiorly of the inner cortical bone after said expansion.

8. The method of claim 1 wherein said positioning forms a plurality of openings and further including inserting a plurality of said fasteners into respective openings and thereafter expanding the expandable sections of said fasteners so as to constrain the relative motion between said first and second bone sections.

* * * * *